United States Patent
Sniadach

(10) Patent No.: US 6,860,270 B2
(45) Date of Patent: Mar. 1, 2005

(54) DOUBLE BARREL VENTILATION MASK FOR A PATIENT

(76) Inventor: Joseph A. Sniadach, 4427 Wynn Rd., Baltimore, MD (US) 21236

(*) Notice: Subject to any disclaimer, the term of this patent is extended or adjusted under 35 U.S.C. 154(b) by 0 days.

(21) Appl. No.: 09/921,365

(22) Filed: Aug. 2, 2001

(65) Prior Publication Data

US 2003/0024530 A1 Feb. 6, 2003

(51) Int. Cl.⁷ .................................................. H04B 1/16
(52) U.S. Cl. ........................ 128/207.14; 128/206.21; 128/206.24; 128/206.27; 128/206.29; 128/207.11; 128/207.18
(58) Field of Search ................... 128/200.24, 201.24, 128/202.15, 203.12, 204.18, 205.13–205.18, 205.25, 206.12–207.18, 200.14, 200.27, 201.23, 201.26, 203.29, 203.28

(56) References Cited

U.S. PATENT DOCUMENTS

| | | | |
|---|---|---|---|
| 2,625,155 A | 1/1953 | Engelder | |
| 2,859,748 A | 11/1958 | Hudson | |
| 3,056,402 A | 10/1962 | Dickinson | |
| 4,328,797 A | 5/1982 | Rollins et al. | |
| 4,470,413 A | 9/1984 | Warncke | |
| 4,559,940 A | 12/1985 | McGinnis | 128/206.26 |
| 4,580,556 A | 4/1986 | Kondur | 128/206.28 |
| 4,848,331 A | 7/1989 | Northway-Meyer | |
| 4,865,027 A | 9/1989 | Laanen et al. | |
| 4,890,609 A | 1/1990 | Wilson, II | 128/206.29 |
| 4,971,053 A | 11/1990 | Tarrats | 128/205.19 |
| 5,197,463 A * | 3/1993 | Jeshuran | 128/207.14 |
| 5,537,994 A * | 7/1996 | Thornton | 128/204.18 |
| 6,405,725 B1 * | 6/2002 | Christopher | 128/200.26 |

* cited by examiner

Primary Examiner—Glenn K. Dawson
(74) Attorney, Agent, or Firm—J. Bruce Hoofnagle

(57) ABSTRACT

A face mask for ventilation of a patient. A face piece is disposed on the patient's face. An oral tube and a nasal tube are disposed through corresponding ports in the face piece. The oral tube extends through the mouth of the patient and the nasal tube extends through the nasal passage of the patient. The ends of the oral tube and the nasal tube are received in the posterior oropharynx of the patient. An adapter is connected to the ends of the oral tube and the nasal tube exteriorly of the face piece. Oxygen is introduced into an inlet port of the adapter wherein the oxygen enters the oral tube and the nasal tube concomitantly and ventilates the patient.

26 Claims, 4 Drawing Sheets

DOUBLE BARREL VENTILATION MASK FOR A PATIENT

CROSS REFERENCE TO RELATED APPLICATION

The present application is related to application Ser. No. 09/920,696 entitled "ADJUSTABLE VENTILATION MASK FOR A PATIENT" which is being filed concurrently herewith.

BACKGROUND OF THE INVENTION

The present invention relates to a face mask for ventilation of a patient and more particularly to a face mask which provides for more direct ventilation as well as concomitant ventilation through both oropharyngeal and nasopharyngeal ports with oral and nasal tubes attached directly to the mask.

RELATED ART

The standard masks currently available for a rescuer or anesthetist attempt to perform the basic function of patient ventilation. A patient who has become unconscious from accidental injury, medical reasons or medications administered requires skilled or relatively untrained medical personnel to provide the basic function of breathing (i.e. ventilation). Many patients are able to be adequately ventilated with the masks currently available; however, there are a significant number of patients who cannot be adequately ventilated. This scenario will lead to anoxic brain injury and death if not quickly addressed. Patients must be ventilated and oxygenated by first responders until paramedics arrive or by hospital personnel until a physician is available to secure the airway usually by tracheal intubation. The patients at increased risk of poor mask ventilation include those who suffer from obesity, obstructive sleep apnea, congenital and acquired facial deformity, patients with beards, facial or airway edema, patients with excessive oral secretions, patients without teeth and occasionally someone who appears an "easy to mask ventilate". Endotracheal intubation can be attempted in these patients; however, this is not immediately available outside of the operating room. The patient's survival depends on the temporizing measure of mask ventilation before tracheal intubation becomes available, and even then these same people are at risk to be "difficult intubations" when compared with the general population. In addition, in many parts of the country where advanced life support is unavailable, endotracheal intubation is not even an option. The final step of providing a surgical airway through an incision in the neck is again a limited option, as most physicians are not skilled in this procedure, and most pre-hospital personnel are not trained to perform this procedure. Death and brain injury are guaranteed results from obstructed airways due to inadequate ventilation.

The problem that occurs in patients who are difficult to mask ventilate often results from inadequate facial seals despite an inflated rim and inadequate delivery of oxygen past redundant oral or pharyngeal tissues which act to block oxygen flow. In an effort to correct these problems, medical personnel may insert a separate oropharyngeal or nasopharyngeal airway, but the rescuer must obtain an adequate facial seal in order for these to function effectively, and usually this remains problematic especially since the basic airway training may be remote and experience limited.

Secondly, if an adequate facial seal is obtained, the rescuer must rely on indirect currents of air passively entering the aforementioned airways from trapping between mask and face. This low-pressured air must not only enter the oropharyngeal or nasopharyngeal airway, but then must have enough force to pass redundant soft tissue in the mouth or oropharynx to enter the trachea.

The applicant is aware of U.S. Pat. No. 3,056,402 to Dickinson which discloses a respiratory mask having a head harness, molded rubber fore piece and pipe for oxygen which is designed for aviation use.

SUMMARY OF THE INVENTION

It is an object of the present invention to provide a mask to improve ventilation and oxygenation to a patient simultaneously through oropharyngeal and nasopharyngeal ports.

It is a further object of the present invention to provide attached oropharyngeal airway with nasopharyngeal airway tract within the face mask which allows for direct airway ventilation and reduces the absolute need of an adequate facial seal, since oropharyngeal and nasalpharyngeal tissues are bypassed.

In accordance with the teachings of the present invention, there is disclosed a face mask for ventilation of a patient, the patient having a mouth, a tongue, a nose and an oropharynx. The face mask has a face piece having a nasal port and an oral port formed therein. A peripheral cuff is formed on the face piece. An oral tube is disposed in the oral port, and when so disposed, the oral tube has a first end extending into the mouth of the patient and a second end extending outwardly from the face piece. A nasal tube is disposed in the nasal port and, when so disposed, the nasal tube has a first end extending into the nose of the patient and a second end extending outwardly from the face piece. An adapter has an inlet end and two outlet ends. One of the outlet ends is removably connected to the first end of the oral tube and the other of the outlet ends is removably connected to the first end of the nasal tube. Means are provided for introducing oxygen into the inlet end of the adapter. In this manner, the patient is ventilated orally and nasally simultaneously through the single inlet.

In further accordance with the teachings of the present invention, there is disclosed a face mask for ventilation of a patent. The face mask has a face piece having two openings formed therein. An oral tube is received in one opening in the face piece, a nasal is tube received in the other opening in the face piece. The oral tube extends through the mouth of the patient to the posterior oropharynx, the nasal tube extends through the nose of the patient to the posterior oropharynx. Means are provided for introducing oxygen into the oral tube and into the nasal tube simultaneously.

In another aspect, there is disclosed a method of ventilating a patient having the following steps. A face piece is provided having an oral port, a nasal port, and peripheral cuff. An oral tube is provided having a first end and a second end. An adapter is provided having an inlet and two outlets. A source of oxygen is provided. The oral tube is connected to the face piece wherein the first end of the oral tube extends inwardly of the face piece and the second end of the oral tube extends outwardly of the face piece. The patient is placed in a supine position lying face up. The second end of the oral tube is placed in the patient's mouth and the face piece is seated on the patient's face wherein the second end of the oral tube rests in the posterior oropharynx and the cuff of the face piece forms a seal with the patient's face. The second end of the nasal tube is inserted in the nasal port wherein the second end of the nasal passes through the nose of the patient and rests in the posterior oropharynx. The nasal tube is seated in the nasal port. One outlet of the adapter is connected to the first end of the oral tube and the other outlet of the adapter is connected to the first end of the nasal tube. Oxygen is introduced into the inlet of the adapter wherein the oxygen passes through the oral tube and the nasal tube simultaneously directly to the posterior oropharynx of the patient such that the patient is ventilated.

These and other objects of the present invention will become apparent from a reading of the following specification, taken in conjunction with the enclosed drawings.

DESCRIPTION OF THE PREFERRED EMBODIMENT

Figure 1:
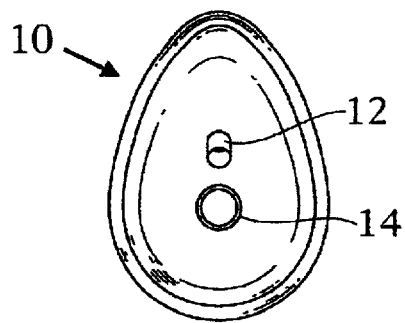
FIG. 1 is a top plan view of the face piece.
Figure 2:
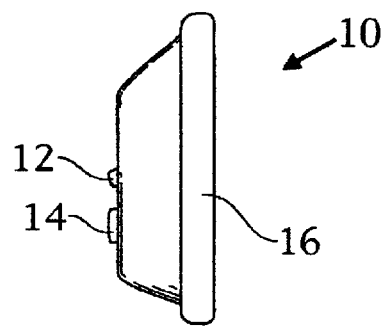
FIG. 2 is a side elevation view of the face piece.
Figure 11:
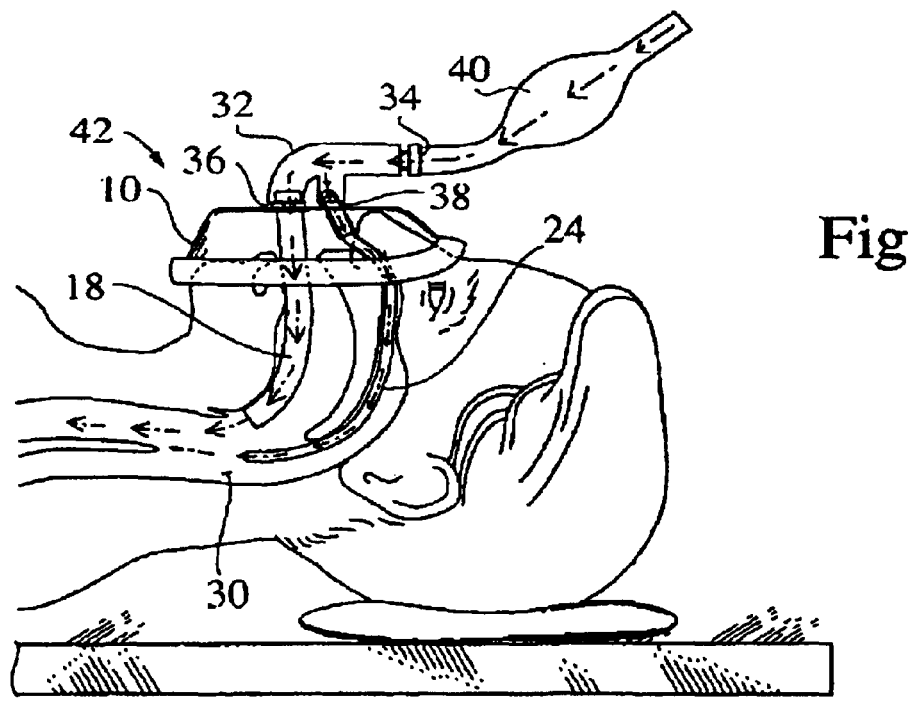
FIG. 11 is a partial cut away view showing oxygen introduced into the ambu bag at the inlet to the adapter ad the oxygen ventilating the patient.
Figure 12:
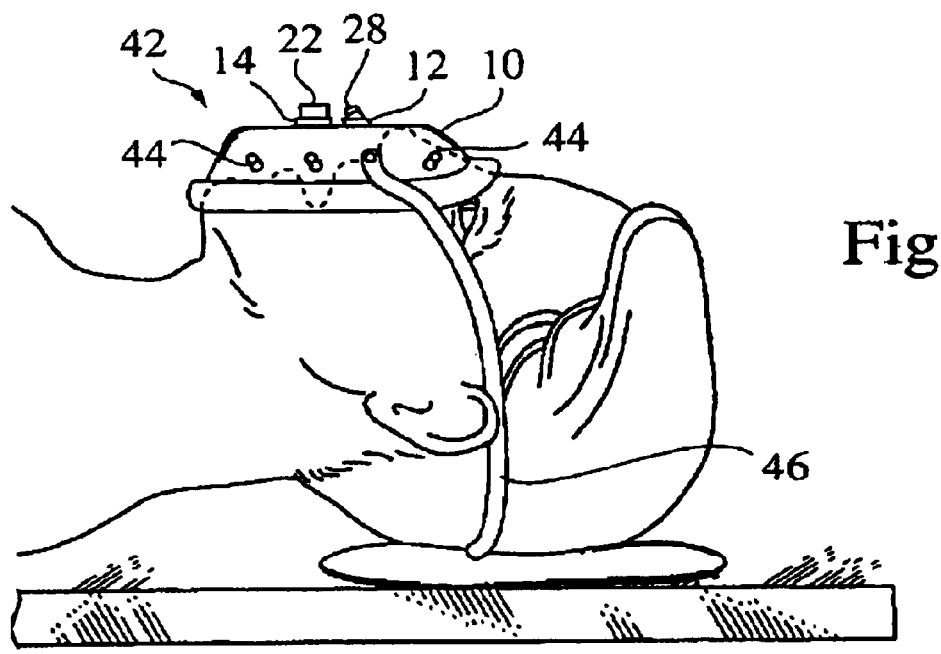
FIG. 12 is a side elevation view of the face mask retained on the face of the patient with protrusions on the face piece and a strap around the patient's head.
Figure 13:
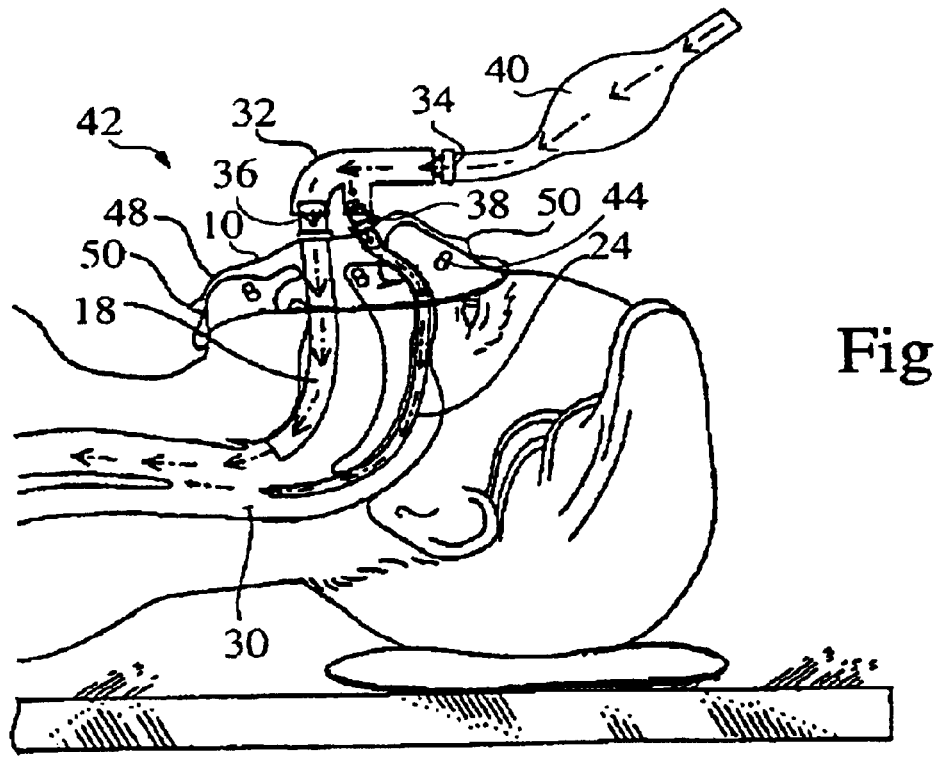
FIG. 13 is partial cutaway view showing the face piece having a chin portion.

Referring now to FIGS. 1 and 2, a face piece 10 has nasal port and an oral port 14 formed therein, which form a portion of a face mask 42 (FIGS. 11, 12 and 13). A peripheral cuff 16 is formed about the face piece 10 to form a seal with the face of the patient when the face mask 42 is placed on the patient's face as will be described. Preferably, the peripheral cuff 16 is padded or inflated, or has a design to form a leak resistant seal with the patient's face. The face piece 10 is preferably formed of an air impermeable material such as rubber, plastic or treated fabric, which preferably is flexible.

Figure 4:
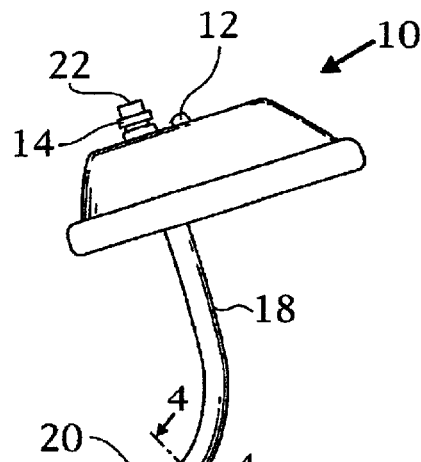
FIG. 4 is a cross sectional view taken along the lines 4—4 of FIG. 3.
Figure 4:
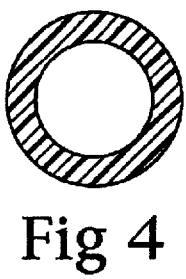
Figure 3:
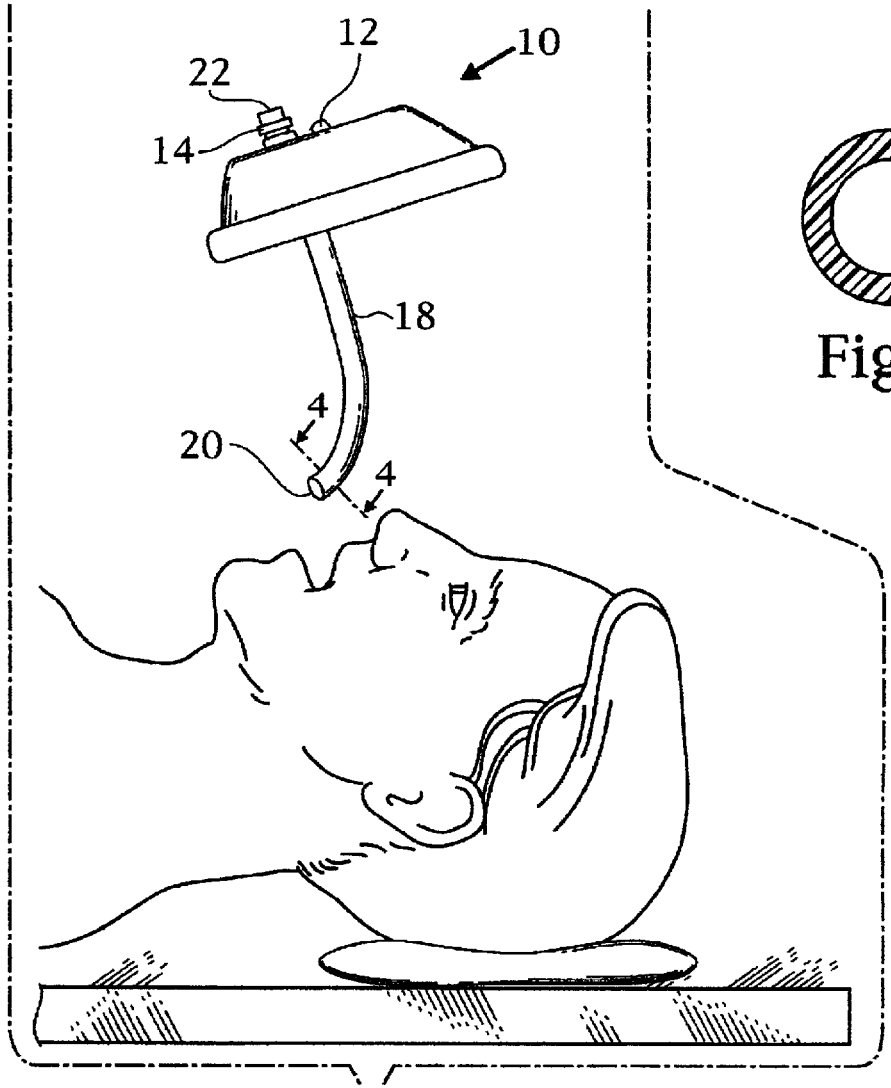
FIG. 3 is a side elevation view of the face piece and oral tube to be mounted on the patient.
Figure 5:
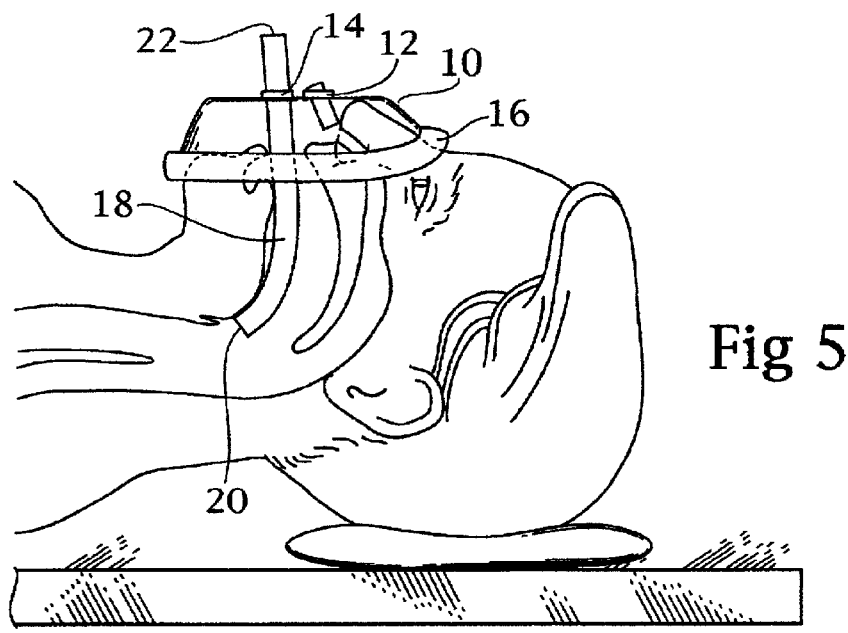
FIG. 5 is a partial cut away view of the face mask and oral tube received by the patient.

A curved oral tube 18 is disposed in the oral port 14 in the face piece 10 (FIGS. 3 and 4). Preferably the oral tube is formed from a rigid material. The oral tube 18 may be permanently connected to the oral port 14 or may be removably connected. The oral port 14 is sealable around the oral tube 18. A first end 20 of the oral tube 18 extends into the mouth of the patient and the second end 22 of the oral tube extends outwardly from the face piece 10. With the patient in a supine, face up position, the oral tube 18 connected to the face piece 10, is placed in the patient's open mouth (FIG. 3) such that the first end 20 of the oral tube 18 rests in the posterior oropharynx 30 of the patient (FIG. 5). When so placed, the oral tube displaces the anterior of the patient's tongue. The length of oral tube 18 may vary depending upon the size of the patient. Small, medium and large lengths of the oral tube 18 may be provided and selected to be more compatible with the patient.

Figure 6:
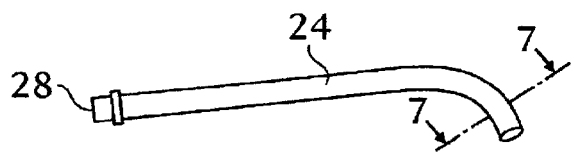
FIG. 6 is a side elevation view of the nasal tube.
Figure 7:
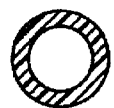
FIG. 7 is a cross sectional view taken along the lines 7—7 of FIG. 6.
Figure 8:
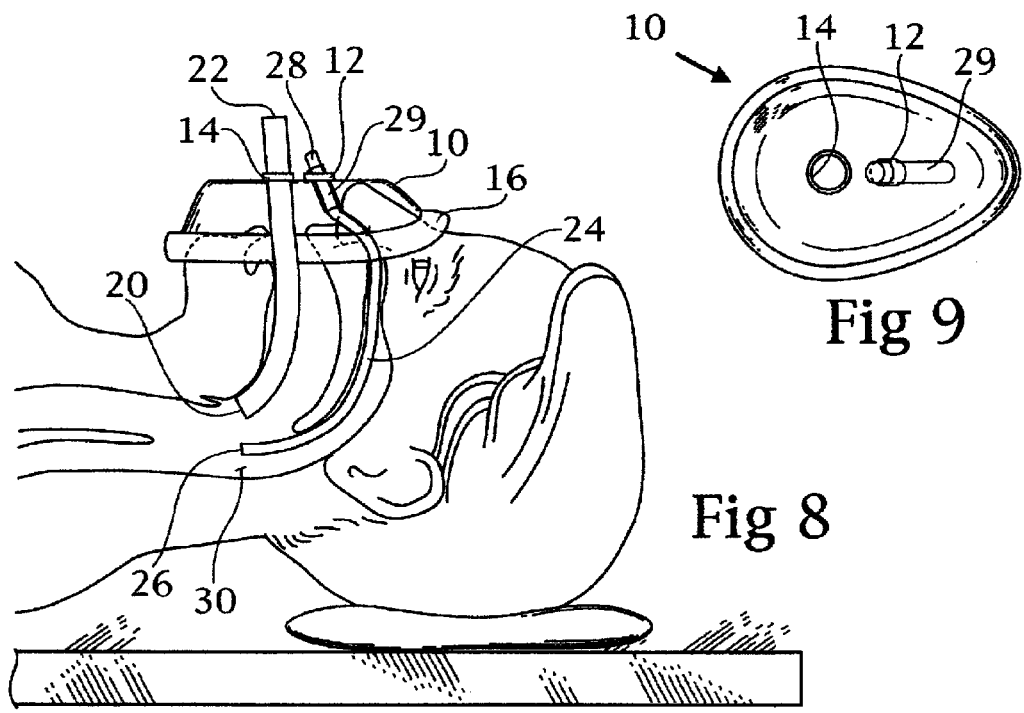
FIG. 8 is a partial cut away view of the face mask with the oral tube and the nasal tube received by the patient.
Figure 9:
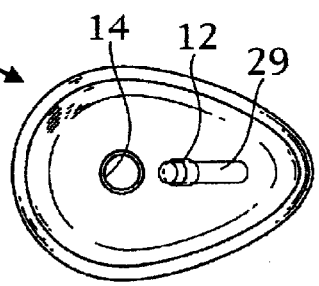
FIG. 9 is a bottom plan view of the face piece showing a sleeve connected to the nasal port.

A curved nasal tube 24 has a first end 26 and an opposite second end 28 (FIGS. 6 and 7). The nasal tube 24 is provided having different internal diameters ranging from 4 mm, 5 mm and 6 mm. The selection of the internal diameter of the nasal tube 24 is determined by the anatomy of the patient on whom the mask is placed. The patient is measured from the nasal port 12 on the face piece 10 to the angle of the patient's jaw. As shown in FIG. 8, the first end 26 of the nasal tube 24 is cut to approximate the measurement. Preferably, a standard 15 mm fitting is connected to the second end 28 of the nasal tube 24. It is preferred that the nasal tube be semi-rigid and have a slip resistant exterior surface. The exterior surface may be rubberized. The interior of the face piece 10 may have a sleeve 29 formed therein which connects to the nasal port 14 to assist in directing the nasal tube 24 to the nostril of the patient (FIG. 9). The nasal tube 24 is inserted in the nasal port 14 in the face piece 10 such that the nasal tube 24 passes into a nostril and through the nasal passage. The first end 26 of the nasal tube 24 is disposed in the posterior oropharynx 30 of the patient beyond the tongue. The nasal tube 24 is snugly seated against the face piece 10.

Figure 10:
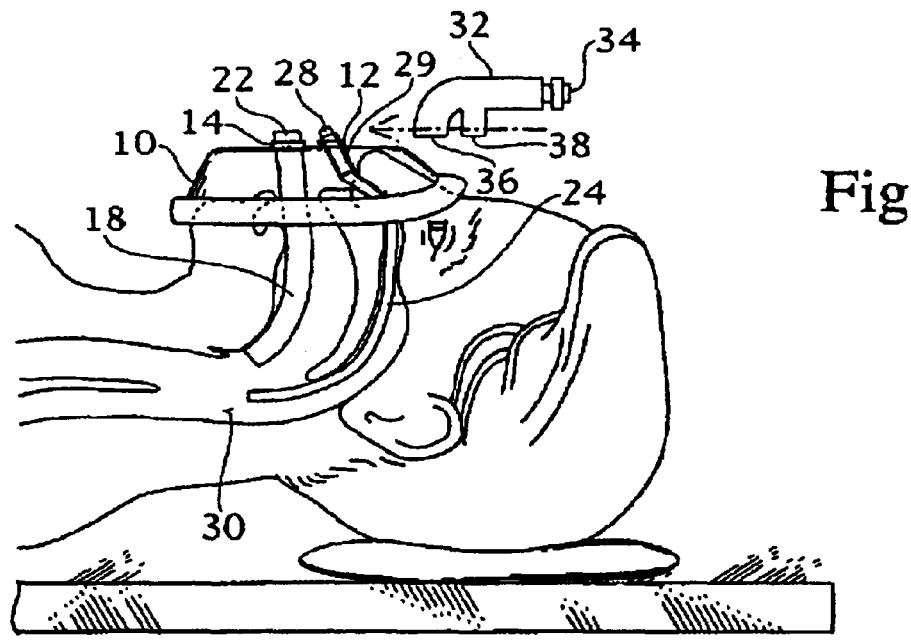
FIG. 10 is a partial cut away view of the adapter being disposed on the oral tube.

An adapter 32 has an inlet end 34, a first outlet end 36 and a second outlet end 38 (FIG. 10). The first outlet end 36 is removably connected to the second end 22 of the oral tube 18 and the second outlet end 38 is removeably connected to the second end 28 of the nasal tube 24. Oxygen may now be introduced into the inlet end 34 of the adapter 32.

Preferably, an ambu bag 40 is connected between the inlet end 34 of the adapter and the source of oxygen (FIG. 11). The ambu bag 40 is pumped to ventilate the patient with the flow of oxygen shown by the arrows.

To further assist in retaining the face mask 42 on the patient, a plurality of spaced apart protrusions 44 are formed on the face piece 10, extending outwardly therefrom (FIG. 12). At least a pair of protrusions 44 are formed on opposite sides of the face piece 10. At least one strap 46 is connected between the at least one pair of protrusions 44 such that the at least one strap 46 is connected to one of the protrusions, extends around the head of the patient and is connected to another of the protrusions of the pair on the opposite side of the face piece 10. There may be more than one strap 46 which is disposed higher or lower on the patient's head in relation to the one strap 46. The strap 46 may be an elastic band which may stretch or may have buckle, hook and loop fasteners or other means known to persons skilled in the art to provide an adjustable length of the strap. In this manner, the strap provides for use with patients having a wide variation in head size.

In a further embodiment, the face piece 10 has a chin portion 48 which encloses the chin of the patient when the face piece is placed on the patient (FIG. 13). This embodiment may also have at least one ridge 50 formed thereon to serve as a grip for the fingers of the rescuer to assist in holding the face piece 10 on the face of the patient.

Thus, the face mask 42 has a face piece 10, an oral tube 18, a nasal tube 24 and an adapter 32. An ambu bag 40 is also preferably, a component of the face mask 42.

The face mask 42 of the present invention provides an improved ability to ventilate marginally ventilated patients and to obtain ventilation on patients who cannot be ventilated by face masks which are presently available. The mask of the present invention has the following features.

1. Concomitant ventilation through both oropharyngeal and nasopharyngeal ports attached directly to the mask.
2. As both oral and nasal ports are connected to the mask, tandem ventilation is achieved directly from a ventilator or from rescuer assisted ventilation.
3. Since air/oxygen is administered directly into the oral and nasal ports which terminate in the oropharynx, difficulty in ventilating through an inadequate facial seal is bypassed. This now, in essence, becomes oropharyngeal ventilation. A mask would essentially not be required, however, its presence can act to prevent oropharyngeal oxygen from escaping in addition to providing the rescuer with facial airway stability.
4. Oxygen, which is being directly administered through ports on the mask, follows continuous tracts into the posterior oropharynx which effectively by-passes redundant oral and oropharyngeal tissues.

Obviously, many modifications may be made without departing from the basic spirit of the present invention. Accordingly, it will be appreciated by those skilled in the art that within the scope of the appended claims, the invention may be practiced other than has been specifically described herein.

What is claimed is:

1. A face mask for ventilation of a patient having a mouth, a tongue, a nose and an oropharynx, the face mask comprising:

a face piece having a nasal port and an oral port formed therein, a peripheral cuff on the face piece, an oral tube disposed in the oral port and, when so disposed, the oral tube having a first end extending into the mouth of the patient and a second end extending outwardly from the face piece, a nasal tube disposed in the nasal port and, when so disposed, the nasal tube having a first end extending into the nose of the patient and a second end extending outwardly from the face piece, an adapter having an inlet end and two outlet end, one of the outlet ends being removably connected to the second end of the oral tube and the other of the outlet ends being removably connected to the second end of the nasal tube, and means for introducing oxygen into the inlet end of the adaptor, wherein the patient is ventilated orally and nasally simultaneously through the single inlet.

2. The face mask of claim 1, wherein the oral tube has a length sufficient to reach the posterior oropharynx of the patient.

3. The face mask of claim 1, wherein the nasal tube has a length sufficient to reach the posterior oropharynx beyond the tongue of the patient.

4. The face mask of claim 1, wherein the nasal tube has an internal diameter in the range of 4 to 6 mm.

5. The face mask of claim 1, wherein a sleeve is connected to the nasal port interiorly of the face piece such that the nasal tube is received in the sleeve and directed to the patient's nostril.

6. The face mask of claim 1, wherein the mask has small, medium and large diameter oral tubes, one of which is selected for the patient.

7. The face mask of claim 1, wherein an ambu bag is connected between the inlet end of the adapter and a source of oxygen such that oxygen may be pumped into the oral tube and the nasal tube to ventilate the patient.

8. The face mask of claim 1, wherein the oral tube is removable.

9. The face mask of claim 1, wherein the nasal tube is removable.

10. A face mask for ventilation of a patient, comprising a face piece, having two openings formed therein, an oral tube received in one opening in the face piece, a nasal tube received in the other opening in the face piece, the oral tube extendable through a mouth of the patient to the posterior oropharynx, the nasal tube extendable through a nose of the patient to the posterior oropharynx, and means for introducing oxygen into the oral tube and into the nasal tube simultaneously.

11. The face mask of claim 10, further having a peripheral cuff thereon, the peripheral cuff forming a seal when the face mask is assembled with a face of the patient.

12. The face mask of claim 10, having an adapter connected to both the oral tube and the nasal tube exteriorly of the face piece, the adapter being connected to a source of oxygen.

13. The face mask of claim 12, wherein an ambu bag is inserted into the adapter and the source of oxygen such that oxygen may be pumped through both the oral tube and the nasal tube to ventilate the patient.

14. The face mask of claim 10, wherein the nasal tube is removable.

15. The face mask of claim 10, wherein the oral tube is removable.

16. The face mask of claim 10, further comprising:

a first protrusion mounted on the face piece, and extending outward from a first location on an external surface of the face piece;

a second protrusion mounted on the face piece, and extending outward from a second location on the external surface of the face piece which is spaced from the first location; and a strap having a first portion connectable to the first protrusion and a second portion, spaced from the first portion, connectable to the second protrusion.

17. The face mask of claim 16, further comprising:

a chin portion which encloses a chin of the patient when the face piece is placed on the face of the patient.

18. The face mask of claim 16, further comprising:

means formed on the face piece for receiving at least one finger of a person placing the face piece on the patient to assist in holding the face piece on the face of the patient.

19. The face mask of claim 16, further comprising:

a chin portion which encloses a chin of the patient when the face piece is placed on the face of the patient, and means formed on the face piece for receiving at least one finger of a person placing the face piece on the patient to assist in holding the face piece on the face of the patient.

20. The face mask of claim 10, further comprising:

a chin portion which encloses a chin of the patient when the face piece is placed on the face of the patient, and means formed on the face piece for receiving at least one finger of a person placing the face piece on the patient to assist in holding the face piece on the face of the patient.

21. The face mask of claim 10, which further comprises:
a chin portion which encloses a chin of the patient of the patient when the face piece is placed on the face of the patient.

22. The face mask of claim 10, which further comprises:
means formed on the face piece for receiving at least one finger of a person placing the face piece on a face of the patient to assist in holding the face piece on the face of the patient.

23. A method of ventilating a patient comprising the steps of
providing a face piece having an oral port, a nasal port, and a peripheral cuff;
providing an oral tube having a first end and a second end,
providing a nasal tube having a first end and a second end,
providing an adapter having an inlet and two outlets,
providing a source of oxygen,
connecting the oral tube to the face piece wherein the first end of the oral tube extends inwardly of the face piece and the second end of the oral tube extends outwardly of the face piece,
placing the patient in a supine position lying face up,
placing the second end of the oral tube in the patient's mouth and seating the face piece on the patient's face wherein the second end of the oral tube rests in the patient's posterior oropharynx and the cuff of the face piece forms a seal with the patient's face,
inserting the second end of the nasal tube in the nasal port wherein the second end of the nasal tube passes through the nose of the patient and rests in the patient's posterior or pharynx and seating the nasal tube in the nasal port,
connecting one outlet of the adapter to the first end of the oral tube and connecting the other outlet of the adapter to the first end of the nasal tube, and
introducing oxygen into the inlet of the adapter wherein the oxygen passes through the oral tube and the nasal tube simultaneously directly to the posterior oropharynx of the patient such that the patient is ventilated.

24. The method of claim 23, further comprising the steps of inserting an ambu bag between the inlet of the adapter and the source of oxygen and pumping the ambu bag to control the introduction of oxygen.

25. The method of claim 23, wherein the nasal tube has a length, measuring a selected portion of the length and cutting off any excess wherein the nasal tube is customized for the patient.

26. A face mask for ventilation of a patient, comprising:
a face piece for placement on a face of the patient, having a first port and a second port formed therein, and
an adapter having an inlet end and two outlet ends, with one of the outlet ends removably connected to the first port and the other of the outlet ends removably connected to the second port, the face piece and the adapter being configured such that ventilation gas delivered through each of the outlet ends and the ports is available for breathing by said patient.

* * * * *